(12) United States Patent
Cooper et al.

(10) Patent No.: US 9,937,153 B2
(45) Date of Patent: Apr. 10, 2018

(54) ORAL PHARMACEUTICAL FORMULATION OF OMARIGLIPTIN

(71) Applicants: Merck Sharp & Dohme Corp., Rahway, NJ (US); Merck Sharp & Dohme Limited, Hoddesdon, Hertfordshire (GB)

(72) Inventors: Vincent Brett Cooper, Cheshunt (GB); Kathryn Alanna Bradley, St Albans (GB); Samuel Robert Pygall, Hoddesdon (GB); Rajan Gupta, Cary, NC (US); Madison Paige Stanford, San Francisco, CA (US); Lin Xie, Long Valley, NJ (US)

(73) Assignees: Merck Sharp & Dohme LTD., Hoddesdon, Hertfordshire (GB); Merck Sharp & Dohme Corp., Rahway, NJ (US)

( * ) Notice: Subject to any disclaimer, the term of this patent is extended or adjusted under 35 U.S.C. 154(b) by 89 days.

(21) Appl. No.: 14/906,085

(22) PCT Filed: Aug. 25, 2014

(86) PCT No.: PCT/US2014/052451
§ 371 (c)(1),
(2) Date: Jan. 19, 2016

(87) PCT Pub. No.: WO2015/031228
PCT Pub. Date: Mar. 5, 2015

(65) Prior Publication Data
US 2016/0166544 A1   Jun. 16, 2016

Related U.S. Application Data

(60) Provisional application No. 61/871,951, filed on Aug. 30, 2013.

(51) Int. Cl.
| *A61K 31/4162* | (2006.01) |
| *A61K 9/20* | (2006.01) |
| *A61K 9/00* | (2006.01) |
| *A61K 47/12* | (2006.01) |
| *A61K 47/26* | (2006.01) |
| *A61K 47/38* | (2006.01) |
| *A61K 9/28* | (2006.01) |

(52) U.S. Cl.
CPC ........ *A61K 31/4162* (2013.01); *A61K 9/0053* (2013.01); *A61K 9/2013* (2013.01); *A61K 9/2018* (2013.01); *A61K 9/2054* (2013.01); *A61K 47/12* (2013.01); *A61K 47/26* (2013.01); *A61K 47/38* (2013.01); *A61K 9/2866* (2013.01)

(58) Field of Classification Search
None
See application file for complete search history.

(56) References Cited

U.S. PATENT DOCUMENTS

| 4,743,450 | A | 5/1988 | Harris |
| 8,143,289 | B2 | 3/2012 | Biftu et al. |
| 2006/0093666 | A1 | 5/2006 | Karki et al. |
| 2012/0201885 | A1* | 8/2012 | Birringer ............... A61K 45/06 424/465 |
| 2013/0109649 | A1* | 5/2013 | Shao .................... C07D 498/04 514/52 |
| 2015/0175609 | A1* | 6/2015 | Biftu .................... C07D 487/04 514/407 |

FOREIGN PATENT DOCUMENTS

| DE | 102007019071 | 10/2008 |
| EP | 0090356 A1 | 7/1987 |
| EP | 1543831 A1 | 6/2005 |
| EP | 2157969 B1 | 8/2012 |
| FR | 2917620 | 12/2008 |
| JP | 2011195557 | 10/2011 |
| WO | WO1996005809 | 2/1996 |
| WO | WO2005009407 A1 | 2/2005 |
| WO | WO2009014676 A1 | 1/2009 |
| WO | WO2010056708 A1 | 5/2010 |
| WO | WO2010115612 A1 | 10/2010 |
| WO | WO2012153347 | 11/2012 |
| WO | WO20120151051 A1 | 11/2012 |
| WO | WO2013003249 A1 | 1/2013 |
| WO | WO2013062902 A2 | 5/2013 |
| WO | WO2013077819 A1 | 5/2013 |
| WO | WO2015031228 A1 | 3/2015 |

OTHER PUBLICATIONS

Bharate et al., Interactions and incompatibilities of pharmaceutical excipients, J. Excipients and Food Chem., pp. 3-26, 1 (3) 2010.
Colaco, C. A. L. S. et al., Pharmaceutical Formulation Instability and the Maillard Reaction, Chemistry Today, 1996, p. 32-37, 00.
Crowley, P. et al., Drug-Excipient Interactions, Pharmaceutical Technology, 2001, p. 1-6, 00.
Crowley, P. J. et al., Wxcipients as stabilizers, Elsevier Science, 1999, p. 237-243, 2, No. 6.
Elmeshad, A. N. et al., Stability studies of the effect of crosslinking on hydrochlorothiazide release, Drug Discovery Ther, 2009, p. 136-142, 3, No. 3.
Hartley, R. F. et al., Degradation Kinetics and Mechanism of an Oxadiazole Derivative, Design of a Stable Drug Product for BMS-708163, a-Secretase Inhibitor Drug Candidate, Journal of Pharmaceutical Sciences, 2012, p. 3124-3133, 101, No. 9.
Kumar, B. P. et al., A Review on Mechanism, Importance and Methods of Compatibility Testing in the Formulation of Dosage Forms, Journal of Chemical and Pharmaceutical Sciences, 2011, p. 141-151, 4, Issue 4.

(Continued)

*Primary Examiner* — Susan T Tran
(74) *Attorney, Agent, or Firm* — Janet E. Fair; Catherine D. Fitch

(57) ABSTRACT

The present invention is directed to stable, oral pharmaceutical formulations of dipeptidyl peptidase-4 inhibitors, such as omarigliptin. Such pharmaceutical formulations comprise omarigliptin; and neutral excipients, wherein the neutral excipient is present in the amount of at least 75% by weight of the pharmaceutical formulation and comprises at least one non-reducible sugar diluent or a mixture of non-reducible sugar diluents.

12 Claims, 1 Drawing Sheet

(56) References Cited

OTHER PUBLICATIONS

Li, S. et al., Effects of Reducing Sugars on the Chemical Stability of Human Relaxin in the Lyophilized State, Journal of Pharmaceutical Sciences, 1996, p. 873-877, 85, No. 8.
Parmar, N. et al., The solution, solid state stability and kinetic investigation in degradation studies of lercanidipine: study of excipients compatibility of lercanidipine, Pharmaceutical Development and Technology, 2012, p. 730-740, 17, No. 6.
Teraoka, R. et al., Effect of Pharmaceutical Excipients on the Stability of Trichlormethiazide Tablets under Humid Conditions, Chem. Phar. Bull, 2009, p. 1343-1347, 57, No. 12.
Waterman, K. C. et al., Hydrolysis in Pharmaceutical Formulations, Pharmaceutical Development and Technology 2002, p. 113-146, 7, No. 2.
Wu, Y. Eta L., Reactive Impurities in Excipients: Profiling, Identification and Mitigation of Drug-Excipient Incompatibility, AAPS PharmSciTech, 2011, p. 1248-1263, 12, No. 4.

* cited by examiner

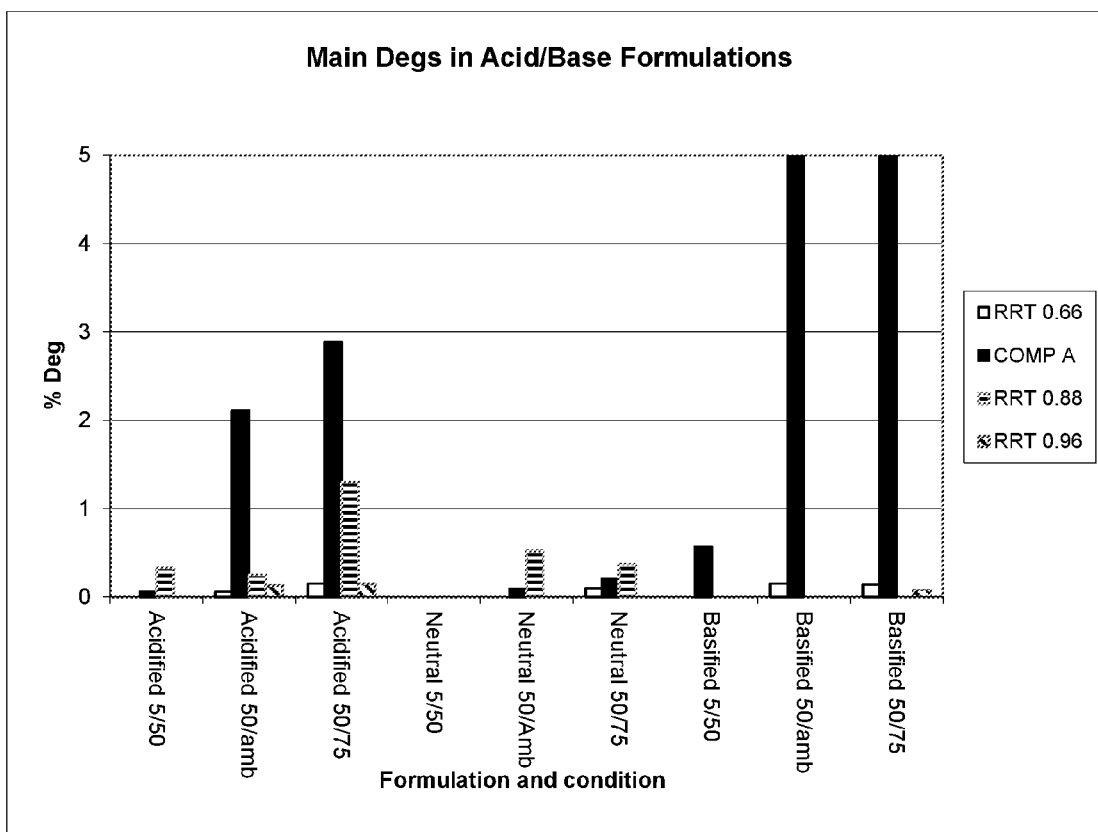

ORAL PHARMACEUTICAL FORMULATION OF OMARIGLIPTIN

CROSS-REFERENCE TO RELATED APPLICATIONS

This application is a U.S. National Phase application under 35 U.S.C. § 371 of PCT Application No. PCT/US2014/052451, filed Aug. 25, 2014, which published as WO2015/031228 A1 on Mar. 5, 2015, and claims priority under 35 U.S.C. § 365(b) from U.S. provisional patent application No. 61/871,951, filed Aug. 30, 2013.

FIELD OF THE INVENTION

The present invention relates to oral pharmaceutical formulations. More particularly, the present invention relate to oral pharmaceutical formulations of dipeptidyl peptidase-4 inhibitors, such as omarigliptin.

BACKGROUND

Inhibition of dipeptidyl peptidase-IV (DP-IV), an enzyme that inactivates both glucose-dependent insulinotropic peptide (GIP) and glucagon-like peptide 1 (GLP-1), is a recognized approach to the treatment and prevention of Type 2 diabetes, also known as non-insulin dependent diabetes mellitus (NIDDM). The therapeutic potential of DP-IV inhibitors for the treatment of Type 2 diabetes has been reviewed: C. F. Deacon and J. J. Holst, "Dipeptidyl peptidase IV inhibition as an approach to the treatment and prevention of Type 2 diabetes: a historical perspective," Biochem. Biophys. Res. Commun, 294: 1-4 (2000); K. Augustyns, et al., "Dipeptidyl peptidase IV inhibitors as new therapeutic agents for the treatment of Type 2 diabetes," Expert. Opin. Ther. Patents, 13: 499-510 (2003); D. J. Drucker, "Therapeutic potential of dipeptidyl peptidase IV inhibitors for the treatment of Type 2 diabetes," Expert Opin. Investig. Drugs, 12: 87-100 (2003); and M. A. Nauck et al., "Incretins and Their Analogues as New Antidiabetic Drugs," Drug News Perspect., 16: 413-422 (2003).

WO 2010/056708 describes a class of aminotetrahydropyrans, which are potent inhibitors of DP-IV and therefore useful for the treatment of Type 2 diabetes. Specifically disclosed in WO 2010/056708 is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine, which is also referred to as omarigliptin. WO2013/003249 describes crystalline forms of (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

A major concern with developing a pharmaceutical formulation with omarigliptin was chemical stability. Due to the functional groups on omarigliptin, degradation was a concern. Thus, there is a need for stable, oral pharmaceutical formulations of omarigliptin.

SUMMARY

The present invention is directed to stable, oral pharmaceutical formulations of dipeptidyl peptidase-4 inhibitors, such as omarigliptin. Such pharmaceutical formulations comprise omarigliptin; and neutral excipients, wherein the neutral excipient is present in the amount of at least 75% by weight of the pharmaceutical formulation and comprises at least one non-reducible sugar diluent or a mixture of non-reducible sugar diluents.

The present invention also provides a process to prepare pharmaceutical compositions described herein by dry or wet processing methods. The dry processing methods include dry compression and dry granulation, and the wet processing methods include wet granulation.

Also described herein are methods of treating diabetes comprising administering to a subject in need thereof, an oral pharmaceutical formulation described herein.

BRIEF DESCRIPTION OF THE DRAWINGS

FIG. 1 shows the amount of degradation that occurs in formulation described herein when spiked with 1% citric acid or $Na_2CO_3$.

DETAILED DESCRIPTION

Unless otherwise specified in this specification, the following terms are defined as follows:

The term "omarigliptin" refers to (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine in any of its forms, such as, amorphous and crystalline.

The phrase "neutral excipients" refers to pharmaceutically acceptable excipients that do not contain an ionic charge. Examples of neutral excipients can include diluents, disintegrants, lubricants, glidants, wetting agents, fillers, surfactants, anti-oxidants and sweeteners.

The phrase "non-reducible sugar diluent" refers the chemical structure of the diluent which contains no reducible sugars. For example the structure of mannitol is:

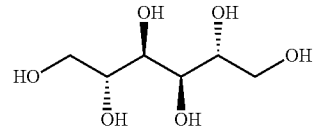 [SMILES: OC[C@@H](O)[C@@H](O)[C@H](O)[C@H](O)CO]

which contains no reducible sugars. However, when procured, an amount of mannitol may contain impurities which may contain reducible sugars. For example, a sample of mannitol may contain impurities in the amount of ≤0.2% by weight. Thus the non-reducible sugar diluent used herein may contain impurities which may contain reducible sugars. In certain, embodiments the pharmaceutical formulations described herein may contain a diluent that contains impurities. For example, the pharmaceutical formulations described herein may contain a diluent that contains impurities in the amount of ≤0.2% by weight.

The term "stable" as used herein refers to a pharmaceutical formulations containing less than 0.5% of each degradant after 1 week at 25° C. at 35% humidity. Common degradants found in pharmaceutical formulations of omarigliptin are Compound A (shown below) and degradants that have a relative retention time of 0.66, 0.88 and 0.96 when undergoing high pressure liquid chromatography.

One concern with developing an oral pharmaceutical formulation of omarigliptin is the chemical stability of the compound. Omarigliptin is sensitive to oxidation, hydrolysis (acid and base catalysed) and Maillard degradation (browning) with reducible sugar impurities in excipients. Also omarigliptin stability is critically sensitive to drug loading with lower drug loadings becoming increasingly unstable in any formulation drug product.

Described herein are oral pharmaceutical formulations that are stable. Such pharmaceutical formulations contain omarigliptin. In certain embodiments, the pharmaceutical formulations contain omarigliptin; and at least 75% neutral excipients comprising a non-reducible sugar diluent or a mixture of non-reducible sugar diluents.

Omarigliptin is an effective dipeptidyl peptidase-4 (DPP-IV) inhibitor that can be administered once weekly. The structure of omarigliptin is shown below:

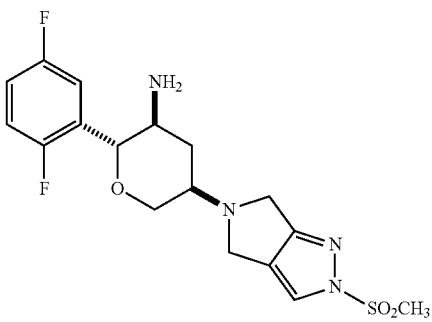

(2R,3S,5R)-2-(2,5-Difluorophenyl)-5-[2-(methylsulfonyl)-2,6-dihydropyrrolo[3,4-c]pyrazol-5(4H)-yl]
tetrahydro-2H-pyran-3-amine Omarigliptin can be synthesized as an amorphous free base or a crystalline free base having Form I, Form II, Form III or Form IV as described in WO2013/003249. In certain embodiments, the omarigliptin used is the amorphous free base or the crystalline free base having Form I, Form II, Form III or Form IV, or a combination thereof. In certain embodiments of the pharmaceutical formulations described herein the omarigliptin used is the amorphous free base. In certain embodiments of the pharmaceutical formulations described herein the omarigliptin used is the crystalline free base having Form I. In certain embodiments of the pharmaceutical formulations described herein the omarigliptin used is the crystalline free base having Form II. In certain embodiments of the pharmaceutical formulations described herein the omarigliptin used is the crystalline free base having Form III. In certain embodiments of the pharmaceutical formulations described herein the omarigliptin used is the crystalline free base having Form IV.

Also described herein are pharmaceutical formulations containing a pharmaceutically acceptable salt of omarigliptin. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Suitable pharmaceutically acceptable salts of omarigliptin include, but are not limited to, fumarate, phosphate and hydrochloride.

Described herein are stable pharmaceutical formulations that contain omarigliptin. In certain formulations described herein a omarigliptin is include, but are not limited to between about 0.25-1 mg, 1-5 mg, 5-10 mg, 10-15 mg, 15-20 mg, 20-25 mg, 25-30 mg, 30-35 mg, 35-40 mg, 40-45 mg and 45-50 mg. The stable omarigliptin formulations described herein can contain, but are not limited to, about 5 mg, 10 mg, 12.5 mg, 15 mg, 17.5 mg, 20 mg and 25 mg of omarigliptin. Preferred embodiments contain a high drug-load of omarigliptin such as 12.5 mg, 15 mg, 17.5 mg, 20 mg and 25 mg of omarigliptin.

The amount of omarigliptin that is contained in the pharmaceutical formulations described herein include, but are not limited to, about 1-5% by weight of the pharmaceutical formulation, 5-10% by weight of the pharmaceutical formulation, 10-15% by weight of the pharmaceutical formulation, 15-20% by weight of the pharmaceutical formulation, 20-25% by weight of the pharmaceutical formulation, 25-30% by weight of the pharmaceutical formulation, 30-35% by weight of the pharmaceutical formulation, 35-40% by weight of the pharmaceutical formulation, 40-45% by weight of the pharmaceutical formulation and 45-50% by weight of the pharmaceutical formulation. For example, the amount of omarigliptin that is contained in the pharmaceutical formulations described herein include, but are not limited to, about 5% by weight of the pharmaceutical formulation, 10% by weight of the pharmaceutical formulation, 15% by weight of the pharmaceutical formulation, 20% by weight of the pharmaceutical formulation, 25% by weight of the pharmaceutical formulation, 30% by weight of the pharmaceutical formulation and 35% by weight of the pharmaceutical formulation. In an embodiment of the pharmaceutical formulations described herein, the amount of omarigliptin is 15.6% by weight of the pharmaceutical formulation. Preferred embodiments have a high drug-load of omarigliptin of about 15% or higher of omarigliptin by weight of the pharmaceutical formulation.

Early formulation work showed that omarigliptin is sensitive to acid and base catalyzed hydrolysis through the pathway shown below:

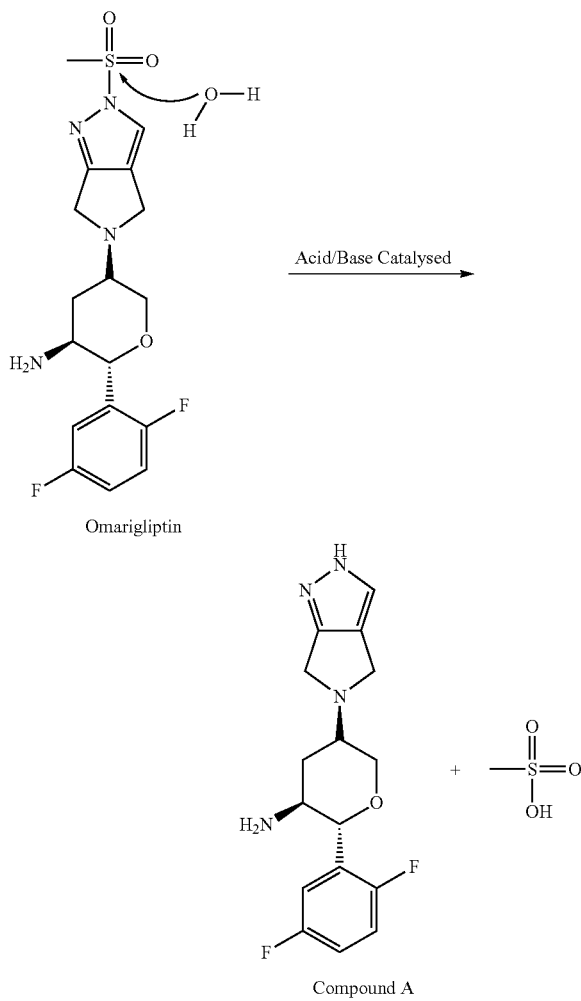

Omarigliptin

Compound A

Thus, the pharmaceutical formulations described herein contain neutral excipients, such as diluents, disintegrants, lubricants, glidants, wetting agents, fillers, surfactants, antioxidants and sweeteners. Neutral excipients are pharmaceutically acceptable excipients that do not possess an ionic charge.

In certain embodiments of the pharmaceutical formulations described herein, the amount of neutral excipients used is at least 60% by weight of the pharmaceutical formulation. In other embodiments of the pharmaceutical formulations described herein, the amount of neutral excipients used is at least 65% by weight of the pharmaceutical formulation. In still other embodiments of the pharmaceutical formulations described herein, the amount of neutral excipients used is at least 68% by weight of the pharmaceutical formulation. In yet other embodiments of the pharmaceutical formulations described herein, the amount of neutral excipients used is at least 70% by weight of the pharmaceutical formulation. In still other embodiments of the pharmaceutical formulations described herein, the amount of neutral excipients used is at least 72% by weight of the pharmaceutical formulation. In other embodiments of the pharmaceutical formulations described herein, the amount of neutral excipients used is at least 75% by weight of the pharmaceutical formulations In other embodiments of the pharmaceutical formulations described herein, the amount of neutral excipients used is at least 80% by weight of the pharmaceutical formulation. In other embodiments of the pharmaceutical formulations described herein, the amount of neutral excipients used is at least 84% by weight of the pharmaceutical formulation.

Additionally formulation work has shown that omarigliptin is sensitive to Maillard degradation with excipients or other impurities that contain reducible sugar impurities. This results in browning. This degradation process with respect to free amines is described in Robertson et al., *Maillard's Reaction and its Impliations for Amine Drugs in the Pharmaceutical Industry*, Digital Edition of American Pharmaceutical Review, Volume 15, Issue 3, April 2012.

Thus, the pharmaceutical formulations containing omarigliptin, described herein do not contain any reducible sugar diluents. In certain embodiments, the pharmaceutical formulations described herein contain a non-reducible sugar diluent or a mixture of non-reducible sugar diluents.

Examples of diluents that are suitable for the pharmaceutical formulations described herein include, but are not limited to, sucrose, mannitol, microcrystalline cellulose, xylitol, maltitol, lactitol, starch, hydroxypropylcellulose (HPC), hydroxypropylmethyl cellulose (HMPC) and sorbitol. Preferred diluents that can be used in the pharmaceutical formulations described herein include, but are not limited to, mannitol and microcrystalline cellulose and mixtures thereof.

Diluents that should not be included in the pharmaceutical formulations described herein include lactose monohydrate, polyvinylpyrrolidone, silicified microcrystalline cellulose, hydroxyethyl cellulose, anhydrous lactose, mannose, glucose, maltose, other reducing sugars, Neusolin, kollidon, crosspovidone and those with acid functional groups or basic functional groups.

In certain embodiments, the pharmaceutical formulations described herein may include diluents in the amount of about 40-90% by weight of the pharmaceutical formulation, 50-90% by weight of the pharmaceutical formulation, 60-90% by weight of the pharmaceutical formulation, 70-90% by weight of the pharmaceutical formulation and 80-90% by weight of the pharmaceutical formulation. In other embodiments, the amount of diluents that are included in the pharmaceutical formulations described herein include, but are not limited to, 40-80% by weight of the pharmaceutical formulation, 50-80% by weight of the pharmaceutical formulation, 60-80% by weight of the pharmaceutical formulation and 70-80% by weight of the pharmaceutical formulation.

In certain embodiments, the amount of diluents that are included in the pharmaceutical formulations described herein include, but are not limited to, about 30-90 mg, 40-90 mg, 50-90 mg, 60-90 mg, 70-90 mg, 80-90 mg. In other embodiments, the amount of diluents that are included in the pharmaceutical formulations described herein include, but are not limited to, about 30-80 mg, 40-80 mg, 50-80 mg, 60-80 mg and 70-80 mg. In other embodiments, the amount of diluents that are included in the pharmaceutical formulations described herein include, but are not limited to, 30-70 mg, 40-70 mg, 50-70 mg and 60-70 mg.

In certain embodiments, the amount of diluents that are included in the pharmaceutical formulations described herein include, but are not limited to, about 60-180 mg, 80-1800 mg, 100-180 mg, 120-180 mg, 140-180 mg, 160-180 mg. In other embodiments, the amount of diluents that are included in the pharmaceutical formulations described herein include, but are not limited to, about 60-160 mg, 80-160 mg, 100-160 mg, 120-160 mg and 140-160 mg. In other embodiments, the amount of diluents that are included in the pharmaceutical formulations described herein include, but are not limited to, about 60-140 mg, 80-140 mg, 100-140 mg and 120-140 mg.

Certain embodiments of the pharmaceutical formulations described herein contain a mixture of diluents, preferably mannitol and microcrystalline cellulose. In certain embodiments, the pharmaceutical formulations described herein, contain about 40-70% by weight of the pharmaceutical formulation of mannitol and about 10-30% by weight of the pharmaceutical formulation of microcrystalline cellulose. In other embodiments, the pharmaceutical formulations described herein, contain about 40-60% by weight of the pharmaceutical formulation of mannitol and about 15-25% by weight of the pharmaceutical formulation of microcrystalline cellulose. In still other embodiments, the pharmaceutical formulations described herein, contain about 50-60% by weight of the pharmaceutical formulation of mannitol and about 20% by weight of the pharmaceutical formulation of microcrystalline cellulose.

In certain embodiments, the pharmaceutical formulations described herein contain a mixture of diluents, preferably mannitol and microcrystalline cellulose. In certain embodiments, the pharmaceutical formulations described herein, contain about 30-60 mg of mannitol and about 10-20 mg of microcrystalline cellulose. In other embodiments, the pharmaceutical formulations described herein, contain about 40-60 mg of mannitol and about 15-20 mg of microcrystalline cellulose. In still other embodiments, the pharmaceutical formulations described herein, contain about 40-50 mg of mannitol and about 16 mg of microcrystalline cellulose.

In certain embodiments, the pharmaceutical formulations described herein, contain a mixture of diluents, preferably mannitol and microcrystalline cellulose. In certain embodiments, the pharmaceutical formulations described herein, contain about 60-120 mg of mannitol and about 20-40 mg of microcrystalline cellulose. In other embodiments, the pharmaceutical formulations described herein, contain about 80-120 mg of mannitol and about 30-40 mg of microcrystalline cellulose. In still other embodiments, the pharmaceutical formulations described herein, contain about 80-100 mg of mannitol and about 32 mg of microcrystalline cellulose.

An exemplary pharmaceutical formulation contains 47.9 mg of mannitol and 16.0 mg of microcrystalline cellulose.

An exemplary pharmaceutical formulation contains 95.8 mg of mannitol and 32.0 mg of microcrystalline cellulose.

The pharmaceutical formulations described herein may also contain one or more lubricants or glidants. Examples of suitable lubricants include magnesium stearate, calcium stearate, stearic acid, sodium stearyl fumarate, hydrogenated castor oil, and mixtures thereof. A preferred lubricant is magnesium stearate. Examples of glidants include colloidal silicon dioxide, calcium phosphate tribasic, magnesium silicate, and talc.

In certain embodiments, the amount of lubricant that is included in the pharmaceutical formulations described herein include, but are not limited to, about 1-5 mg, 1-4 mg and 1-3 mg. In certain embodiments, the amount of lubricant that is included in the pharmaceutical formulations described herein include, but are not limited to, about 2-10 mg, 2-8 mg and 2-6 mg.

The amount of lubricant that is contained in the pharmaceutical formulations described herein include, but are not limited to, 2-5% by weight of the pharmaceutical formulation, 2-4% by weight of the pharmaceutical formulation and 2-3% by weight of the pharmaceutical formulation. In certain examples of the pharmaceutical formulations described herein, the amount of lubricant that is contained in the pharmaceutical formulations described herein is 2.5% by weight of the pharmaceutical formulation.

The amount of lubricant used in the pharmaceutical formulations described herein is important to establish a formulation that would provide satisfactory elegance while maintaining adequate tensile strength, disintegration, and friability. An amount of lubricant of about 2% or more by weight of the pharmaceutical formulation provided satisfactory elegance while maintaining adequate tensile strength, disintegration, and friability. For example, an amount of lubricant of about 2.5% by weight of the pharmaceutical formulation provided satisfactory elegance while maintaining adequate tensile strength, disintegration, and friability.

The pharmaceutical compositions of the present invention may also optionally contain a disintegrant. The disintegrant may be polycarboxylic acids, such as croscarmellose sodium, sodium starch glycollate, polacrillin potassium, and carboxymethylcellulose calcium (CMC Calcium). In one embodiment, the disintegrant is croscarmellose sodium. Croscarmellose sodium NF Type A is commercially available under the trade name "Ac-di-sol."

The pharmaceutical formulations described herein may also optionally contain one or more neutral surfactants or wetting agents. Neutral surfactants include glyceryl monooleate, polyoxyethylene sorbitan fatty acid esters, polyvinyl alcohol, and sorbitan esters. Embodiments of wetting agents include poloxamer, polyoxyethylene alkyl ethers, polyoxyethylene castor oil derivatives, and polyoxyethylene stearates.

An anti-oxidant may optionally be added to the formulation to impart chemical stability. The anti-oxidant is selected from the group consisting of α-tocopherol, γ-tocopherol, δ-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), and butylated hydroxyanisole (BHA). In one embodiment, the antioxidant is BHT or BHA.

Preferred dosage forms for the pharmaceutical formulations described herein are tablets which are prepared by compression methods. Such tablets may be film-coated such as with a mixture of hydroxypropylcellulose and hydroxypropylmethylcellulose containing titanium dioxide and/or other coloring agents, such as iron oxides, dyes, and lakes; a mixture of polyvinyl alcohol (PVA) and polyethylene glycol (PEG) containing titanium dioxide and/or other coloring agents, such as iron oxides, dyes, and lakes; or any other suitable immediate-release film-coating agent(s). The coat provides taste masking and additional stability to the final tablet. A commercial film-coat is Opadry® which is a formulated powder blend provided by Colorcon.

Finally, a sweetening agent and/or flavoring agent may be added if desired.

In one embodiment of the pharmaceutical formulations described herein, the pharmaceutical formulation comprises 15-16% by weight of omarigliptin, 77-82% by weight of a non-reducible sugar diluent or mixture of non-reducible sugar diluents wherein the diluent or mixture of diluents, 2% by weight of a disintegrant, and 2.5% by weight of a lubricant.

In one embodiment of the pharmaceutical formulations described herein, the pharmaceutical formulation comprises 15-16% by weight of omarigliptin, 77-82% by weight of a mixture of mannitol and microcrystalline cellulose, 2% by weight of croscarmellose sodium and 2.5% by weight of magnesium stearate.

The following Table shows additional embodiments of the pharmaceutical formulations described herein:

TABLE 1

| Formulation Ingredient | 12.5 mg potency (%) | 25 mg potency (%) |
|---|---|---|
| Omarigliptin | 15.6% | 15.6% |
| Mannitol | 59.9% | 59.9% |
| Microcrystalline Cellulose | 20% | 20% |
| Croscarmellose sodium | 2% | 2% |
| Magnesium stearate | 2.5% | 2.5% |
| Opadry 20A | 6% | 4% |
| Carnuba Wax | 0.01% | 0.01% |
| Tablet weight without coating | 80 mg | 160 mg |
| Total coated tablet weight mg | 84.8 mg | 166.4 mg |

In one embodiment of the pharmaceutical formulations described herein, the pharmaceutical formulation comprises 12.5 mg of omarigliptin, 63.9 mg of a non-reducible sugar diluent or mixture of non-reducible sugar diluents, 1.6 mg of a disintegrant, 2.0 mg of a lubricant.

In one embodiment of the pharmaceutical formulations described herein, the pharmaceutical formulation comprises 12.5 mg of omarigliptin, 47.9 mg of mannitol and 16.0 mg of microcrystalline cellulose, 1.6 mg of croscarmellose sodium and 2.0 mg of magnesium searate.

In one embodiment of the pharmaceutical formulations described herein, the pharmaceutical formulation comprises 25.0 mg of omarigliptin, 127.8 mg of a non-reducible sugar diluent or mixture of non-reducible sugar diluents, 3.2 mg of a disintegrant, 4.0 mg of a lubricant.

In one embodiment of the pharmaceutical formulations described herein, the pharmaceutical formulation comprises 25.0 mg of omarigliptin, 95.8 mg of mannitol and 32.0 mg of microcrystalline cellulose, 3.2 mg of croscarmellose sodium and 4.0 mg of magnesium searate.

The pharmaceutical formulations described herein can be prepared by wet or dry processing methods. In certain embodiments the pharmaceutical formulations are prepared by wet processing methods, such as but not limited to wet granulation methods. With wet granulation either high-shear granulation or fluid-bed granulation may be used. In one embodiment fluid-bed granulation is employed which has the advantage of affording tablets with higher diametric strength.

In other embodiments, the pharmaceutical formulations can be prepared by dry processing methods such as but not limited to direct compression or dry granulation methods. An example of dry granulation is roller compaction.

The pharmaceutical formulations obtained by the dry or wet processing methods may be compressed into tablets, encapsulated, or metered into sachets.

EXAMPLES

Example 1: Excipient Stability Data

A high throughput excipient screen was performed for omarigliptin that contained a mix of binary mixtures as well as some pre-designed formulation blends. The chemical stability of the plates was assessed after 4-weeks at 40° C./75% relative humidity in open plates. A summary of the potential risk findings for the excipients used in the screen are listed in Table 3.

TABLE 2

| Low Risk (≤1% Total Degradation) | Medium Risk (≥1% but ≤3.5% Total Degradation) | High Risk (≥3.5% Total Degradation) |
|---|---|---|
| Magnesium stearate | Avicel PH102 | Dibasic calcium phosphate |
| Sodium stearyl fumerate | HPC EXF | Croscarmellose sodium |
| Stearic acid | Kaolin | Crospovidone |
| | Lactitol | HPMC |
| | Mannitol | Neusilin |
| | Sorbitol | SMCC (Prosolv) |
| | StarCap | Sodium Starch glycolate |
| | Starch 1500 | Kollidon VA-64 |
| | Sucrose | |

Example 2: Formulation of Omarigliptin

Table 3 shows two formulations of omarigliptin. The first is a tablet formulation comprising 12.5 mg of omarigliptin the second is a tablet formulation comprising 25.0 mg of omarigliptin.

TABLE 3

| | | | Unit Strength/Image | |
|---|---|---|---|---|
| Components | Compendial Testing | Function | 12.5 mg mg/tablet | 25 mg mg/tablet |
| omarigliptin | — | Active | 12.5 | 25.0 |
| Mannitol | Compendial† | Diluent | 47.9 | 95.8 |
| Microcrystalline Cellulose | Compendial† | Diluent | 16.0 | 32.0 |
| Croscarmellose Sodium | Compendial† | Disintegrant | 1.6 | 3.2 |
| Magnesium Stearate, [Non-Bovine] | Compendial† | Lubricant | 2.0 | 4.0 |
| Tablet Core Weight | | | 80.0 | 160.0 |
| Opadry ® Yellow 20A92710§ | — | Film coating mixture | 4.8 | N/A‡ |
| Opadry ® Blue 20A99172# | — | Film coating mixture | N/A‡ | 6.4 |
| Opadry ® White 20A18334¶ | — | Film coating mixture | N/A‡ | N/A‡ |

TABLE 3-continued

| Components | Compendial Testing | Function | Unit Strength/Image 12.5 mg mg/tablet | 25 mg mg/tablet |
|---|---|---|---|---|
| Carnauba Wax | Compendial† | Film coating mixture | 0.008 | 0.016 |
| Coated Tablet Weight | | | 84.808 | 166.416 |

§Opadry® Yellow 20A92710 is purchased from Colorcon and consists of the following ingredients: HPMC 2910/hypromellose, hydroxypropyl cellulose, titanium dioxide, Talc, and iron oxide yellow.
Opadry® Blue 20A99172 is purchased from Colorcon and consists of the following ingredients: HPMC 2910/hypromellose, hydroxypropyl cellulose, titanium dioxide, and FD&C Blue #2/Indigo carmine aluminum lake.
†Opadry® White 20A18834 is purchased from Colorcon and consists of the following ingredients: HPMC 2910/hypromellose, hydroxypropyl cellulose, and titanium dioxide.

Methods of Manufacturing

The above 25-mg and 12.5-mg tablets listed in Table 1 are manufactured by blending omarigliptin and the other excipients, lubricating with magnesium stearate, followed by compression and subsequent film coating.

Example 3: Formulation Spiked with 1% Citric Acid or Na₂CO₃

Samples were made with 1% Citric Acid or Na₂CO₃ by first coating a mortar with mannitol. Omarigliptin was then triturated using the mortar and pestle with 0.1000 g mannitol then with 0.1000 g mannitol & 0.1000 g citric acid or Na₂CO₃ and then with equal amounts mannitol. The triturate was added to the remaining ingredients and blended initially with mortar and pestle and then transferred into a glass bottle and blended with a blender at medium speed for 15 mins. Magnesium stearate was passed through a 250 micron screen and the required quantity was dispensed and added to the powders in the bottle. The mixture was blended for 1 minute at medium speed. Tablets were compressed using a press having ¼" normal concave punches at 100 mg unit weight:

FIG. 1 shows that when the formulation is spiked with 1% citric acid or Na₂CO₃ degradation occurs. The most common degradants where Compound A (COMP A) and a degradant with a relative retention time (RRT) of 0.66, a degradant with a relative retention time (RRT) of 0.88 and a degradant with a relative retention time (RRT) of 0.96 using high pressure liquid chromatography (HPLC).

Example 4: Comparative Salt Stability after 1 Week at 50° C.

Fumarate, phosphate and hydrochloride salts of omarigliptin were made and used in the manufacture of pharmaceutical formulations as described in Example 3. The pharmaceutical formulations containing the fumarate, phosphate and hydrochloride salts of omarigliptin as well as pharmaceutical formulations containing the free base were tested under various conditions for stability. The results are provided in Table 4.

TABLE 4

| Condition | % Area | % LC | Total Degs. (Area %) | Salt |
|---|---|---|---|---|
| 5° C./50% RH closed | 98.8 | 88.5 | — | Free Base I |
| 5° C./50% RH closed | 95.9 | 79.6 | — | Fumerate |
| 5° C./50% RH closed | 96.8 | 76.5 | — | Phosphate |
| 5° C./50% RH closed | 98.69 | 75.5 | — | HCl |
| 50° C./closed | 97.9 | 85.9 | 0.9 | Free Base I |
| 50° C./closed | 94.3 | 75.9 | 1.6 | Fumerate |
| 50° C./closed | 94.0 | 70.8 | 2.9 | Phosphate |
| 50° C./closed | 97.6 | 71.8 | 1.3 | HCl |
| 50° C./75% RH/open | 97.1 | 82.0 | 1.7 | Free Base I |
| 50° C./75% RH/open | 93.8 | 69.5 | 2.0 | Fumerate |
| 50° C./75% RH/open | 92.0 | 54.4 | 4.8 | Phosphate |
| 50° C./75% RH/open | 95.3 | 62.5 | 3.6 | HCl |

Example 5: Optimization of Lubricant

Elegance

Tablets were made as described in Example 3 with 1%, 2%, 2.5% and 3% by weight of the pharmaceutical formulation of magnesium stearate. 20 tablets of each batch were inspected by two people (10 tablets each) according to OSD3067 CF. Major defects were not observed. For 80-mg tablets, 2.5% magnesium stearate demonstrated satisfactory elegance. For 160-mg tablets, 2% magnesium stearate demonstrated satisfactory elegance. A confirmatory batch of 160-mg and 80-mg tablets was produced with 2.5% magnesium stearate following the magnesium stearate optimization studies, and no defects were observed during batch manufacture.

What is claimed is:

1. A tablet composition comprising, by weight of the composition:
   15-16% omarigliptin; and
   77-82% mixture of non-reducible sugar diluents.
2. The tablet of claim 1, wherein the amount of omarigliptin is 12.5 mg or 25 mg.
3. The tablet of claim 1, wherein the mixture of non-reducible sugar diluents comprises microcrystalline cellulose and mannitol.
4. The tablet of claim 1, wherein the tablet further comprises a lubricant.
5. The tablet of claim 4, wherein the lubricant is magnesium stearate.
6. The tablet of claim 4, wherein the lubricant is present in the amount of 2.5% by weight of the tablet.
7. The tablet of claim 1, wherein the tablet further comprises a disintegrant.

8. The tablet of claim 7, wherein the disintegrant is croscarmellose sodium.

9. The tablet of claim 7, wherein the tablet further comprises a coating.

10. A method of treating diabetes comprising administering the tablet of claim 1, to a subject in need thereof.

11. The method of claim 10, wherein the tablet of claim 1 is administered once weekly.

12. A stable oral pharmaceutical formulation consisting essentially of:

| | |
|---|---|
| Omarigliptin | 15.6% |
| Mannitol | 59.9% |
| Microcrystalline Cellulose | 20% |
| Croscarmellose sodium | 2% |
| Magnesium stearate | 2.5%. |

* * * * *